US00PP12132P2

(12) United States Plant Patent
Hensler

(10) Patent No.: US PP12,132 P2
(45) Date of Patent: Oct. 9, 2001

(54) *VINCA MINOR* PLANT NAMED 'ILLUMINATION'

(76) Inventor: Christy Ann Hensler, 952 Viet Rd., Newport, WA (US) 99156-9325

( * ) Notice: Subject to any disclaimer, the term of this patent is extended or adjusted under 35 U.S.C. 154(b) by 0 days.

(21) Appl. No.: 09/332,956

(22) Filed: Jun. 14, 1999

(51) Int. Cl.[7] ..... A01H 5/00
(52) U.S. Cl. ..... Plt./226
(58) Field of Search ..... Plt./226

(56) References Cited

U.S. PATENT DOCUMENTS

P.P. 6,960 * 8/1989 MacKenzie ..... Plt./226
P.P. 8,170 * 3/1993 Perrine ..... Plt./226

OTHER PUBLICATIONS

UPOV–ROM GTITM Computer database 2000/04, GTI JOUVE Retrieval Software, citation for "Illumination", Aug. 2000.*

* cited by examiner

*Primary Examiner*—Bruce R. Campell
*Assistant Examiner*—W A Baker

(57) ABSTRACT

A new *Vinca minor* cultivar named 'Illumination' is characterized primarily by the unique variegation of its foliage. The mature foliage has creamy yellow centers surrounded by dark green margins. The stems of 'Illumination' are greyed purple in color when mature.

2 Drawing Sheets

BACKGROUND OF THE INVENTION

This new invention presents a distinct cultivar of a *Vinca minor* and will be referred to hereafter by the cultivar name 'Illumination'. *Vinca minor* is an evergreen, suffrutiscent creeping vine that is used commercially as a ground cover.

The new cultivar was discovered in the inventor's garden in Newport, Wash. in 1995. 'Illumination' was isolated from a branch sport arising in a patch of common, green-leafed *Vinca minor* (unpatented). It is distinguished by it's variegated foliage consisting of yellow to cream colored centers surrounded by dark green margins. The mature stems are also unique in that they are greyed purple in color.

No other known cultivar, known to the inventor, has a coloration that is similar to this new cultivar 'Illumination'. There are two cultivars of periwinkle that are available in the trade with gold variegation; 'Golden' and 'Blue and Gold', both of which have thin gold margins and green centers. Another cultivar, 'Valley Glow', has leaves that emerge a gold color, but then the leaves turn green upon maturation.

The original asexual propagation of 'Illumination' was done by the inventor in Newport, Wash. using compound layering of the branch sport in the spring of 1995. The new cultivar has subsequently been propagated by stem cuttings and has remained stable and true to type in successive generations since it's discovery.

SUMMARY OF THE INVENTION

The new cultivar 'Illumination' is unique and unlike any other lesser periwinkle known to the inventor. The coloration and pattern of the variegation is the primary distinguishing characteristic of this new cultivar. The variegation is stable and is comprised of creamy colored centers with dark green margins. There is some variation in the pattern and central color during leaf maturation. The young, emerging foliage has bright green centers. As the leaves mature, the centers become more yellow in color and finally mature to a creamy yellow. The center coloration typically comprises 75–85% of the leaf area. The stems mature to a greyed purple color that is not usually observed in the species. The flowers are lavender-blue which is typical for the species. These traits in combination distinguish this periwinkle as a unique cultivar.

BRIEF DESCRIPTION OF THE DRAWING

The first drawing illustrates a plant as grown in a one-gallon container grown under greenhouse conditions in Encinitas Calif. The second drawing is of a one-year old plant of 'Illumination' in bloom that was grown under partial sunlight in the garden. The colors in these photographs are as true as possible by conventional photography.

BOTANICAL DESCRIPTION OF THE PLANT

The following traits have been repeatedly observed and are the basic characteristics of the cultivar 'Illumination'. General growth observations describe this plant as grown outdoors in Newport, Wash. Botanical data was taken from a mature plant in a one-gallon container that was grown from three rooted cuttings for one year under greenhouse conditions in Encinitas, Calif. The color codes are in reference to The R.H.S. Colour Chart of The Royal Horticultural Society.

Botanical classification: 'Illumination' is a cultivar of *Vinca minor.*

Commercial classification: Lesser Periwinkle

Type: Hardy, evergreen, suffrutiscent creeping vine. Grown as a groundcover.

Origin: Branch sport of common *Vinca minor.*

Propagation: Layering or stem cuttings (leaf and node). Crown division is also possible.

Growth habit: Prostrate, creeping. Stems arise vertically from the crown and may Stay erect and reach a height of 15–20 cm but they typically elongate into a vine of indeterminate length. The vine stems become prostrate as they elongate and form infrequent branches.

Hardiness: Plants have survived temperature of −29° F. Hardy in Zones 4–9.

Vigor: Grows readily in sun and shade and soils of reasonable fertility and moisture, However, the best coloration is observed when grown in the shade or part shade in moist, but well-drained soil; excessive sunlight may wash-out the color or scorch the leaves. A single rooted 2" plug placed under garden conditions in Washington for four months will increase in crown diameter by 6–8" with vines reaching a length of 3–5'.

Bloom season: Blooms in early-mid spring and sporadically later in the season.

Disease resistance/susceptibility: No known disease problems have been observed.

Stems: Suffrutiscent (woody at the base and more herbaceous terminally), round and have diameters of 2 mm, color is green (145C) when young, changes to a dull salmon (173C) as they mature and are typically a greyed purple color (184C) at maturity. This dull salmon and greyed purple coloration is also observed in early spring on the base of the stems when the new stems are emerging. Branching occurs sporadically. Internodes: 1.4 to 3.0 cm in length.

Foliage:

*Division.*—Simple.

*Shape.*—Ovate.

*Arrangement.*—Opposite.

*Size.*—1.5 to 2.0 cm in length, 0.6 to 1.5 cm in width.

*Attitude.*—slightly curved, leaf blades are concave.

*Apex.*—Obtuse.

*Base.*—Obtuse.

*Insertion.*—Petiolate (petioles are curved so that the opposite leaves are on the same plane and held above the stem, petiole color is 145C).

*Venation.*—Not prominent.

*Color.*—Emerging leaves have bright green centers (144B), that change to a yellow-green (151B) and finally turn a creamy yellow at maturation (10A). The center color typically occupies from 75 to 85% of the total leaf surface with rare occurrences of lower than 50% coverage. The margins are a deep green color (139A) throughout maturation. Small, irregular, medium green 143C blotches often exist between the margins and centers and are insignificant at maturation.

Flowers:

*Type.*—Salverform, solitary.

*Size.*—2 to 2.7 cm in diameter, 2 cm deep.

*Corolla.*—Lavender blue (93C), 5-petalled, sympetalous, irregular, non-overlapping. Lobes are 1.1–1.2 cm in length, 0.4 cm to 1.1 cm at tip in width, orifice 5 mm.

*Calyx.*—Asepalous.

*Pistil.*—Single, included.

*Stamens.*—Pentandrous, included, adnate to corolla.

Fruit/Seeds: Not observed. The small, cylindrical fruit follices of *Vinca minor* are very rarely ever observed in cultivation.

I claim:

1. A new and distinct variety of *Vinca minor* plant, as herein illustrated and described.

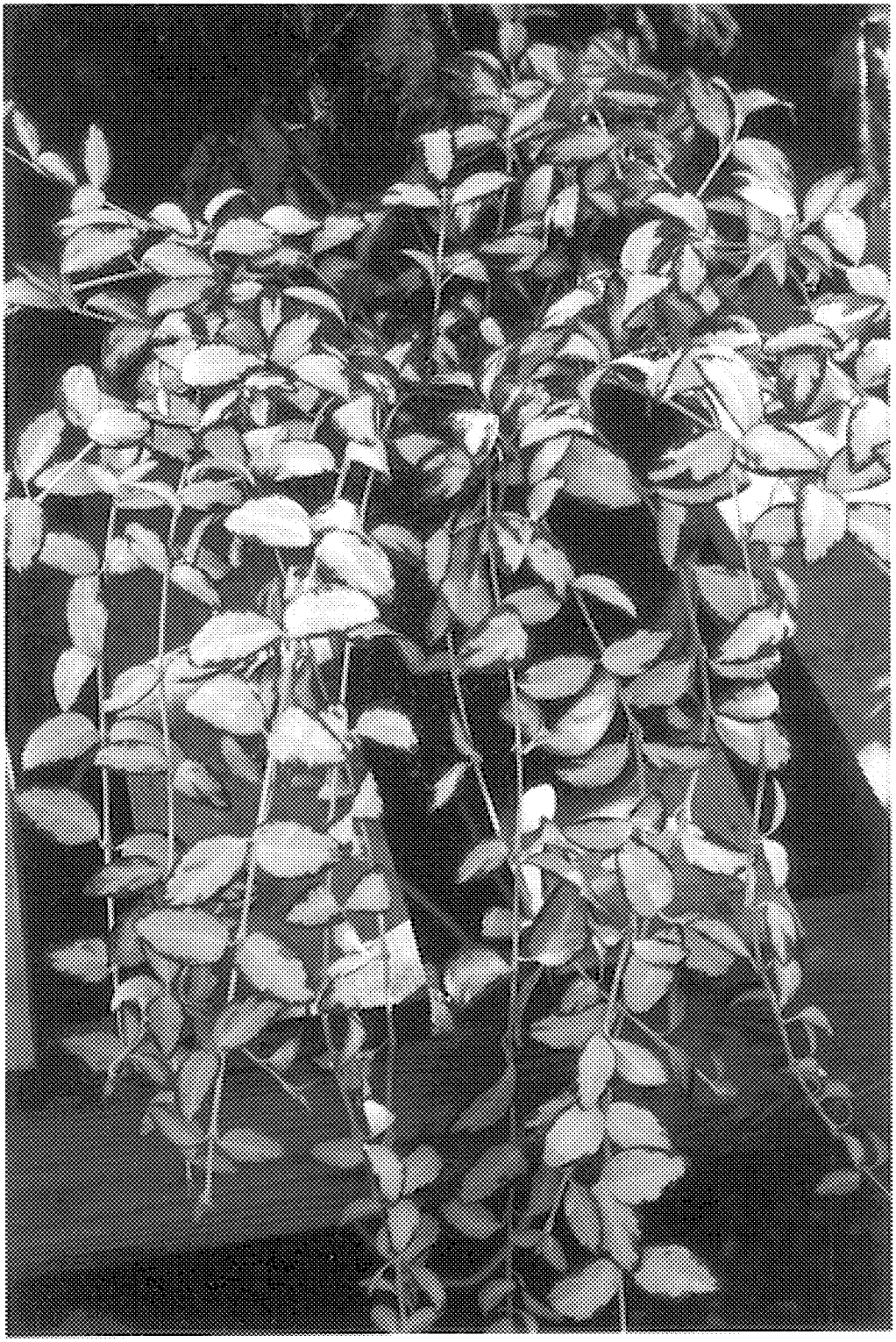

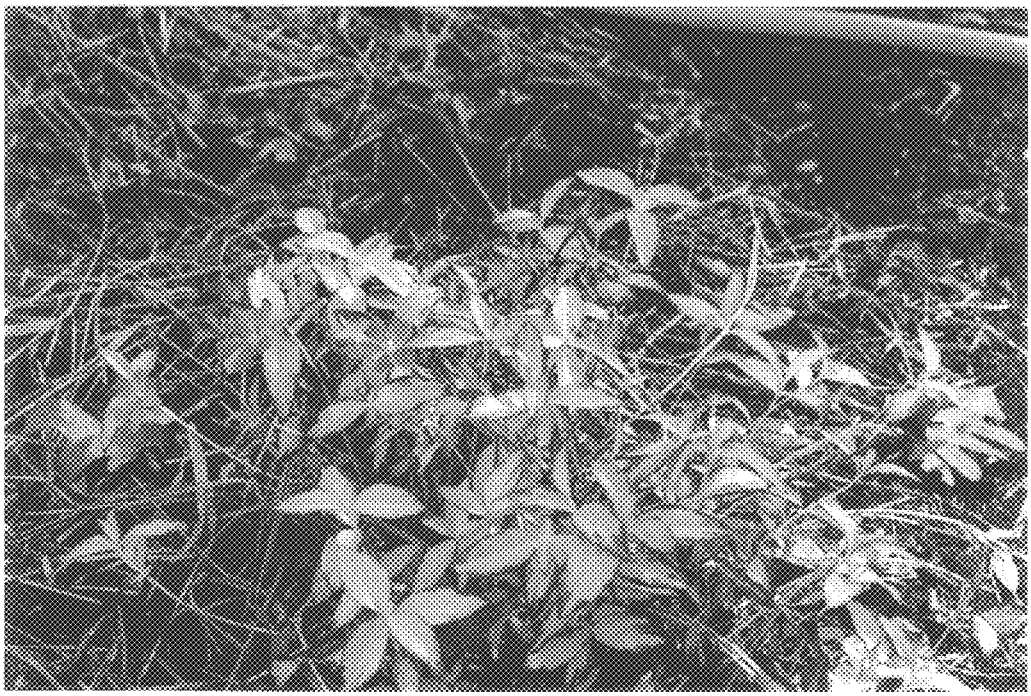

* * * * *